United States Patent [19]

Holtkamp

[11] Plant 4,373

[45] Feb. 6, 1979

[54] AFRICAN VIOLET PLANT

[75] Inventor: Reinhold Holtkamp, Isselburg, Fed. Rep. of Germany

[73] Assignee: Geselischaftsvertrag uber die Erfindergemeinschaft "OPTIMARA", Isselburg, Fed. Rep. of Germany

[21] Appl. No.: 911,296

[22] Filed: May 31, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African Violet known by the cultivar name Alabama and particularly characterized by its flower color, which is predominantly white, with blue-purple centers and edges, wavy and frilled flower edges; vigorous growth habit, and by its flower production, with up to 10 individual flowers being carried on each flower stem.

1 Drawing Figure

The present invention comprises a new and distinct cultivar of African Violet plant, botanically known as *Saintpaulia ionantha,* hereinafter referred to by the cultivar name Alabama. Alabama is a product of a planned breeding program, and was referred to during the breeding and selection process by the number 89/78.

The new cultivar was originated from a cross made in a controlled breeding program in Isselburg, Rhineland, Germany. The female, or seed parent, was an unpatented cultivar identified as 288/4 blue-white, and the male, or pollen parent, also unpatented, was identified as 30/1 blue. Alabama was discovered and selected as a flowering plant within the progeny of the stated cross by me in a controlled environment in Isselburg, Rhineland, Germany, and subsequent asexual reproduction of the new cultivar by leaf cuttings and by division of shoots as performed by me at such location, has demonstrated that the combination of characteristics as herein disclosed for the new cultivar are firmly fixed and are retained through successive generations of asexual reproduction.

The following characteristics have been repeatedly observed and are determined to be the basic characteristics of Alabama, which in combination distinguish this African Violet as a new and distinct cultivar:

1. The flower petals are predominantly white and have a violet-blue center portion, with the same color appearing on the wavy and frilled edges of the flower.
2. Each flower comprises three relatively large and two relatively smaller petals which together provide a generally symmetrical, violet-shaped flower.
3. The peduncles are slightly bent and rigid, with the plant in full bloom having seven or more peduncles each of which carries up to 10 individual flowers.
4. Alabama possesses excellent growth characteristics, with the cultivar being in full bloom approximately 10–12 weeks after potting of the small plantlet.

The accompanying photographic drawing comprises a perspective view of a typical specimen plant of the new cultivar. The colors appearing in the photograph are as true as possible with color illustrations of this type.

In the following description, color references are made to the Royal Horticultural Society Color Chart (RHS), 1966 edition, except where general color terms of ordinary significance are employed. The observations, measurements and values describe plants grown in Isselburg, Rhineland, Germany, under greenhouse conditions which closely approximate those generally used in commercial practice.

Botanical classification: *Saintpaulia ionantha,* Ramat cv. Alabama.

Parentage:

*Male parent.*—30/1 blue.

*Female parent.*—288/4 blue-white.

Propagation: The new cultivar holds its distinguishing characteristics through successive propagations by leaf cuttings and by division of shoots.

Plant: From 10 cm. to 12 cm. tall when grown in pots, and approximately 30 cm. in diameter when fully grown.

Leaves:

*General form.*—Generally round tending toward oblong.

*Diameter.*—80 mm. at largest dimension.

*Texture.*—Rough, very hairy.

*Aspect.*—Edges slightly serrated.

*Veins.*—Very well pronounced on both upperside and underside of leaf.

*Color (upperside).*—Green, 137 B.

*Color (underside).*—142 C.

*Petiole.*—Light green-yellow.

Flowers:

*Buds.*—round, diameter 7–9 mm., color 142 C.

*Sepals.*—five; 5 mm. long, spear-shaped. Color: light green. Calyx: seed bud grown together with receptacle. Aspect: funnel shaped. Peduncle: Slightly bent, wiry.

Individual flowers:

*Size.*—The flower is up to 40 mm. in diameter.

*Color.*—Upperside: base color white, 155 C, center and edge between 88 C and 89 C. Underside: base color white, 155 C, center and edge 88C.

*Borne.*—The flower stems carry up to nine single flowers.

*Shape.*—Five petals; three relatively large, 22 mm. long and 18 mm. wide, and two smaller, 19 mm. long and 16 mm. wide.

*Arrangement.*—Flowers are on slightly bent flower stems, with up to 10 blossoms on each stem.

*Flowering time.*—7–8 weeks after potting, the first flowers appear; after 10–12 weeks, the plant is in full bloom.

Reproductive organs:

*Stamens.*—Two in number.

*Anthers.*—4 anthers, color 7 B.

*Arrangement.*—The stamens are connected to the receptacle by two short, flat stems.

*Filaments.*—3–4 mm. long, flat and wide.

*Styles.*—7–8 mm. long.

*Pollen color.*—7 C.

Roots: The young plants have well developed and branched out root systems; young root tips are white, turning brownish when older.

Disease resistance: No disease problems noticed to date.

General observations: Alabama is a very fast growing and vigorous African Violet with up to 9 peduncles, and up to 10 individual flowers carried on each peduncle. The principle flower color is white, with the center of the flower being blue-violet, with the frilled edges of the flower petals likewise being blue-violet. The flowers are durable and non-dropping, and after 10–12 weeks cultivation, Alabama is in full bloom.

I claim:

1. A new and distinct cultivar of African Violet known by the cultivar name Alabama and particularly characterized as to uniqueness by its flower color, which is predominantly white, with blue-purple centers and edges; wavy and frilled flower edges; vigorous growth habit, and by its flower production, with up to 10 individual flowers being carried on each flower stem.

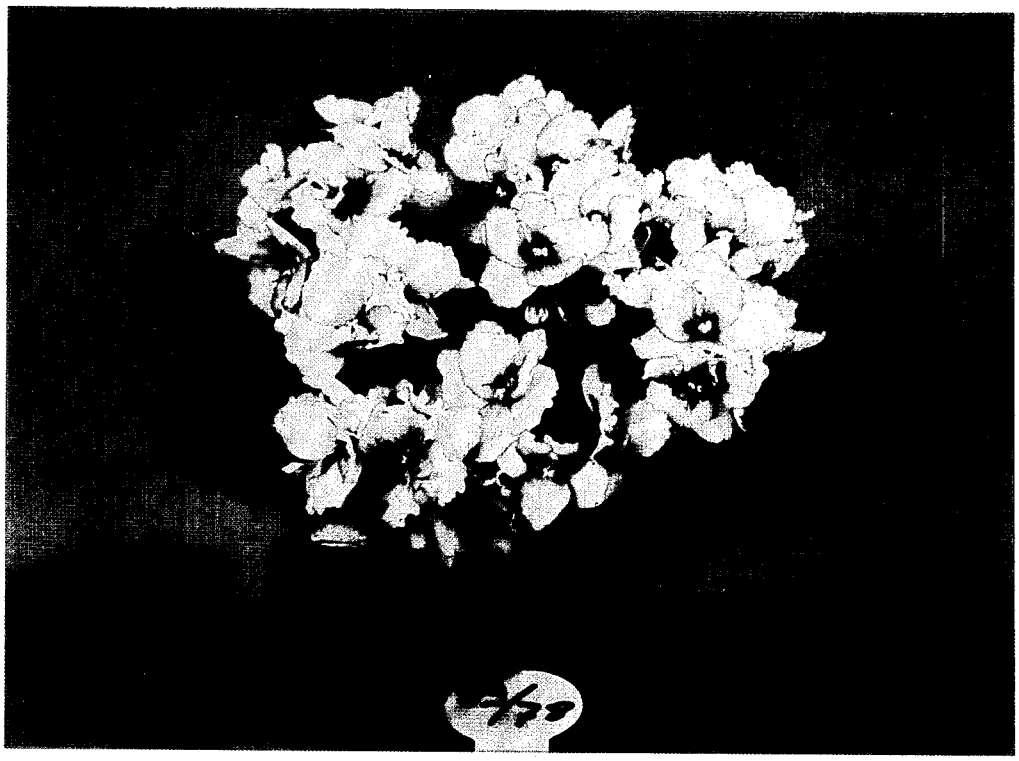

* * * * *